United States Patent
Hubbard, Jr.

(10) Patent No.: US 10,045,890 B2
(45) Date of Patent: Aug. 14, 2018

(54) OPEN CELL FOAM ASSOCIATED WITH A SECOND OPEN CELL FOAM

(71) Applicant: The Procter & Gamble Company, Cincinnati, OH (US)

(72) Inventor: Wade Monroe Hubbard, Jr., Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 364 days.

(21) Appl. No.: 14/750,399

(22) Filed: Jun. 25, 2015

(65) Prior Publication Data
US 2015/0374560 A1 Dec. 31, 2015

(30) Foreign Application Priority Data
Jun. 27, 2014 (EP) .................................... 14174682

(51) Int. Cl.
*A61F 13/53* (2006.01)
*B01J 20/28* (2006.01)
*B01J 20/26* (2006.01)
*A61L 15/42* (2006.01)
*A61L 15/22* (2006.01)
*A61L 15/60* (2006.01)

(52) U.S. Cl.
CPC .............. *A61F 13/53* (2013.01); *A61L 15/22* (2013.01); *A61L 15/425* (2013.01); *A61L 15/60* (2013.01); *B01J 20/26* (2013.01); *B01J 20/28045* (2013.01); *A61F 2013/530649* (2013.01)

(58) Field of Classification Search
CPC ........ A61L 15/22; A61L 15/425; A61L 15/60; A61F 13/53; A61F 2013/530649
See application file for complete search history.

(56) References Cited

U.S. PATENT DOCUMENTS

| | | | | |
|---|---|---|---|---|
| 5,037,859 A | * | 8/1991 | Williams, Jr. | .......... C04B 28/24 521/134 |
| 5,817,704 A | * | 10/1998 | Shiveley | .................. A61F 13/53 521/63 |
| 5,856,366 A | | 1/1999 | Shively et al. | |
| 6,642,430 B1 | * | 11/2003 | Busam | .............. A61F 13/15658 604/368 |
| 2012/0108692 A1 | * | 5/2012 | Dyer | ..................... C08F 220/18 521/149 |

FOREIGN PATENT DOCUMENTS

EP 1048276 11/2000

OTHER PUBLICATIONS

Lepine, O. et al., "Preparation of Macrocellular PU-PS Interentrating Networks", Polymer, Elsevier Science Publishers B.V., GB, vol. 46 No. 23, Nov. 14, 2005, pp. 9653-9663.
PCT International Search Report, PCT/US2015/037851, dated Aug. 14, 2015, 10 pages.

* cited by examiner

*Primary Examiner* — Hai Vo
(74) *Attorney, Agent, or Firm* — Andres E. Velarde

(57) ABSTRACT

An absorbent structure having a first open cell foam associated with a second open cell foam.

9 Claims, 5 Drawing Sheets

OPEN CELL FOAM ASSOCIATED WITH A SECOND OPEN CELL FOAM

FIELD OF THE INVENTION

The present invention relates to absorbent structures useful in absorbent articles such as diapers, incontinent briefs, training pants, diaper holders and liners, sanitary hygiene garments, and the like. Specifically, the present invention relates to an absorbent structure utilizing a first open cell foam having a cellular structure which is associated with a second open cell foam.

BACKGROUND OF THE INVENTION

Open celled foams are used for their absorbent properties. Open celled foams include latex polymer foams, polyurethane foams, and foams created by polymerizing an emulsion. One type of an open celled foam is created from an emulsion that is a dispersion of one liquid in another liquid and generally is in the form of a water-in-oil mixture having an aqueous or water phase dispersed within a substantially immiscible continuous oil phase. Water-in-oil (or oil in water) emulsions having a high ratio of dispersed phase to continuous phase are known in the art as High Internal Phase Emulsions, also referred to as "HIPE" or HIPEs. Different foams may be chosen due to specific properties.

Traditionally foams are either used as a carrier for other materials or are homogeneous within the foam. However, different foams may serve different purposes. Specifically, by associating a first open cell foam with a second open cell foam, foams may be chosen for specific properties to create one absorbent structure.

Therefore there exists a need to create an absorbent structure that has a first open cell foam that is associated with a second open cell foam.

SUMMARY OF THE INVENTION

An absorbent structure comprising a first open cell foam and a second open cell foam, wherein the first open cell foam is associated with the second open cell foam.

An absorbent structure comprising a first open cell foam and a second open cell foam, wherein the first open cell foam provides a cellular structure comprising the second open cell foam.

An absorbent article comprising a topsheet, a backsheet, and an absorbent core wherein the absorbent core comprises an absorbent structure comprising a first open cell foam and a second open cell foam, wherein the first open cell foam is associated with the second open cell foam.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
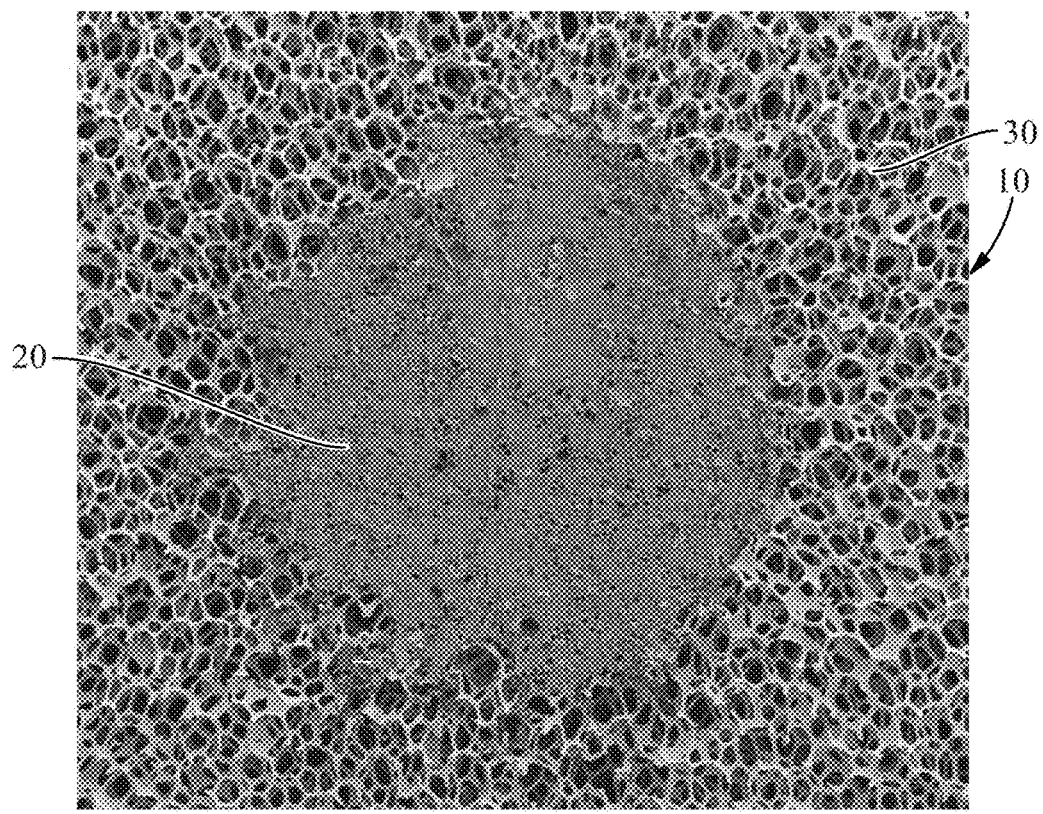
FIG. 1 shows a magnified cross section view of foam cellular structure containing a HIPE foam.

As used herein, the term "associated" describes that the first item is connected with something else. Association may occur due to entanglement, enrobing, direct contact, linking, connection, or mechanical connection. Association as used herein excludes the use of adhesives.

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin or a panty liner. The absorbent structure of the present invention will be herein described in the context of a typical absorbent article, such as, for example, a sanitary napkin. Typically, such articles can comprise a liquid pervious topsheet, a backsheet and an absorbent core intermediate the topsheet and the backsheet.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

While particular embodiments of the present invention have been illustrated and described, it would be obvious to those skilled in the art that various other changes and modifications can be made without departing from the spirit and scope of the invention.

GENERAL SUMMARY

An absorbent structure is disclosed. The absorbent structure has a first open cell foam that has a cellular structure and a second open cell foam that has a cellular structure. The second open cell foam is associated with the first open cell foam. The second open cell foam is associated with the first open cell foam in that at least a portion of the second open cell foam is in intimate contact with at least a portion of the first open cell foam. In a non-limiting embodiment, the second open cell foam may be mechanically engaged to the first open cell foam. In a non-limiting embodiment, the first open cell foam cellular structure may contain the second open cell foam.

The absorbent structure has a depth, a width, and a height. The absorbent structure may be used as any part of an absorbent article including, for example, a part of an absorbent core, as an absorbent core, and/or as a topsheet for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. The absorbent structure may be used in any product utilized to absorb and retain a fluid including surface wipes. The absorbent structure may be used as a paper towel. Exemplary absorbent articles in the context of the present invention are disposable absorbent articles.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The absorbent structure may exhibit an absorbency of between 10 g/g to 200 g/g of the, such as for example, between 20 g/g and 190 g/g of the absorbent structure, such as, for example 30 g/g, 40 g/g, 60 g/g, 80 g/g, 100 g/g, 120 g/g, 140 g/g 160 g/g 180 g/g or 190 g/g of the absorbent structure. Absorbency may be quantified according to the Edana Absorption method 10.4-02.

Dependent upon the desired foam composite density, polymer composition, specific surface area, or pore size (also referred to as cell size), the first open cell foam and the second open cell foam may be made with different chemical composition, physical properties, or both. For instance, dependent upon the chemical composition, an open celled foam may have a density of 0.0010 g/cc to about 0.25 g/cc. Preferred 0.04 g/cc.

The first open cell foam and the second open cell foam have pore sizes that may range in average diameter of from 1 to 800 μm, such as, for example, between 50 and 700 μm, between 100 and 600 μm, between 200 and 500 μm, between 300 and 400 μm.

In an embodiment, the pores of the first open cell foam may be a percentage of the pore size of the second open cell foam such as, for example, between 0.03% and 99%. In an embodiment the average pore size of the first open cell foam may be between 0.03% and 99% of the average pore size of the second open cell foam, such as, for example, 0.1%, 0.5%, 1%, 1.5%, 2%, 5%, 10%, 20%, 30%, 40%, 50%, 60%, 70%, 80%, or 90%.

In an embodiment, the pores of the second open cell foam may be a percentage of the pore size of the first open cell foam such as, for example, between 0.03% and 99%. In an embodiment the average pore size of the second open cell foam may be between 0.03% and 99% of the average pore size of the first open cell foam, such as, for example, 0.1%, 0.5%, 1%, 1.5%, 2%, 5%, 10%, 20%, 30%, 40%, 50%, 60%, 70%, 80%, or 90%.

In some embodiments, the first open cell foam, second open cell foam, or both may have a cellular structure that has a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface.

In an embodiment, the first open cell foam is polymerized before being introduced to an unpolymerized second open cell foam. The second open cell foam may be inserted into or placed onto the first open cell foam prior to polymerization.

In a non-limiting embodiment, the first open cell foam may contain the second open cell foam within the first open cell foam. The second open cell foam may be contained within the cell structure of the first open cell foam.

In a non-limiting embodiment, the first open cell foam and the second open cell foam may be associated at a barrier layer. The second open cell foam may permeate into the first open cell foam cellular structure. The second open cell foam may fracture the first open cell foam during polymerization.

The cellular structure produced from the first open cell foam and the second open cell foam is relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 μm in average diameter size are in fluid communication with at least one adjoining cell.

In addition to being open-celled, in certain embodiments the absorbent structure is sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

In certain embodiments, for example when used in certain absorbent articles, the absorbent structure may be flexible and exhibit an appropriate glass transition temperature (Tg). The Tg represents the midpoint of the transition between the glassy and rubbery states of the polymer.

In certain embodiments, the Tg of the absorbent structure will be less than about 200° C. for foams used at about ambient temperature conditions, in certain other embodiments less than about 90° C. The Tg may be less than 50° C.

In certain embodiments, the first open cell foam or the second open cell foam may be flexible and exhibit an appropriate glass transition temperature (Tg). The Tg represents the midpoint of the transition between the glassy and rubbery states of the polymer.

In certain embodiments, the Tg of the first open cell foam or the second open cell foam will be less than about 200° C. for foams used at about ambient temperature conditions, in certain other embodiments less than about 90° C. The Tg may be less than 50° C.

In a non-limiting embodiment, the first open cell foam, second open cell foam, or both open cell foams may include any suitable thermoplastic polymer, or blend of thermoplastic polymers, or blend of thermoplastic and non-thermoplastic polymers.

Examples of polymers, or base resins, suitable for use in the foam polymer formula include styrene polymers, such as polystyrene or polystyrene copolymers or other alkenyl aromatic polymers; polyolefins including homo or copolymers of olefins, such as polyethylene, polypropylene, polybutylene, etc.; polyesters, such as polyalkylene terephthalate; and combinations thereof. A commercially available example of polystyrene resin is Dow STYRON® 685D, available from Dow Chemical Company in Midland, Mich., U.S.A.

Coagents and compatibilizers can be utilized for blending such resins. Crosslinking agents can also be employed to enhance mechanical properties, foamability and expansion. Crosslinking may be done by several means including electron beams or by chemical crosslinking agents including organic peroxides. Use of polymer side groups, incorporation of chains within the polymer structure to prevent polymer crystallization, lowering of the glass transition temperature, lowering a given polymer's molecular weight distribution, adjusting melt flow strength and viscous elastic properties including elongational viscosity of the polymer melt, block copolymerization, blending polymers, and use of polyolefin homopolymers and copolymers have all been used to improve foam flexibility and foamability. Homopolymers can be engineered with elastic and crystalline areas. Syndiotactic, atactic and isotactic polypropylenes, blends of such and other polymers can also be utilized. Suitable polyolefin resins include low, including linear low, medium and high-density polyethylene and polypropylene, which are normally made using Ziegler-Natta or Phillips catalysts and are relatively linear; generally more foamable are resins having branched polymer chains. Isotactic propylene homopolymers and blends are made using metallocene-based catalysts. Olefin elastomers are included.

Ethylene and α-olefin copolymers, made using either Ziegler-Natta or a metallocene catalyst, can produce soft, flexible foam having extensibility. Polyethylene cross-linked with α-olefins and various ethylene ionomer resins can also be utilized. Use of ethyl-vinyl acetate copolymers with other polyolefin-type resins can produce soft foam. Common modifiers for various polymers can also be reacted with chain groups to obtain suitable functionality. Suitable alkenyl aromatic polymers include alkenyl aromatic homopolymers and copolymers of alkenyl aromatic compounds and copolymerizable ethylenically unsaturated comonomers including minor proportions of non-alkenyl aromatic polymers and blends of such. Ionomer resins can also be utilized.

Other polymers that may be employed include natural and synthetic organic polymers including cellulosic polymers, methyl cellulose, polylactic acids, polyvinyl acids, polyacrylates, polycarbonates, starch-based polymers, polyetherimides, polyamides, polyesters, polymethylmethacrylates, and copolymer/polymer blends. Rubber-modified polymers such as styrene elastomers, styrene/butadiene copolymers, ethylene elastomers, butadiene, and polybutylene resins, ethylene-propylene rubbers, EPDM, EPM, and other rubbery homopolymers and copolymers of such can be added to enhance softness and hand. Olefin elastomers can also be utilized for such purposes. Rubbers, including natural rubber, SBR, polybutadiene, ethylene propylene terpolymers, and vulcanized rubbers, including TPVs, can also be added to improve rubber-like elasticity.

Thermoplastic foam absorbency can be enhanced by foaming with spontaneous hydrogels, commonly known as superabsorbents. Superabsorbents can include alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, carboxy-methylcellulose, isobutylene maleic anhydride copolymers, and mixtures thereof. Further suitable polymers include inorganic polymers, such as polyphosphazene, and the like. Furthermore, thermoplastic foam biodegradability and absorbency can be enhanced by foaming with cellulose-based and starch-based components such as wood and/or vegetable fibrous pulp/flour.

In addition to any of these polymers, the foam polymer formula may also, or alternatively, include diblock, triblock, tetrablock, or other multi-block thermoplastic elastomeric and/or flexible copolymers such as polyolefin-based thermoplastic elastomers including random block copolymers including ethylene a-olefin copolymers; block copolymers including hydrogenated butadiene-isoprene-butadiene block copolymers; stereoblock polypropylenes; graft copolymers, including ethylene-propylene-diene terpolymer or ethylene-propylene-diene monomer (EPDM), ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Polymers of Belpre, Ohio, U.S.A., under the trade designation KRATON® elastomeric resin or from Dexco, a division of ExxonMobil Chemical Company in Houston, Tex., U.S.A., under the trade designation VECTOR® (SIS and SBS polymers) or SEBS polymers as the SEPTON® series of thermoplastic rubbers from Kuraray America, Inc. in New York, N.Y., U.S.A.; blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E.I. Du Pont de Nemours in Wilmington, Del., U.S.A., under the trade name LYCRA® polyurethane, and ESTANE® available from Noveon, Inc. in Cleveland, Ohio, U.S.A.; thermoplastic elastic polyamides, including polyether block amides available from ATOFINA Chemicals, Inc. in Philadelphia, Pa., U.S.A., under the trade name PEBAX® polyether block amide; thermoplastic elastic polyesters, including those available from E.I. Du Pont de Nemours Company, under the trade name HYTREL®, and ARNITEL® from DSM Engineering Plastics of Evansville, Ind., U.S.A., and single-site or metallocene-catalyzed polyolefins having a density of less than about 0.89 grams/cubic centimeter such as metallocene polyethylene resins, available from Dow Chemical Company in Midland, Mich., U.S.A. under the trade name AFFINITY™; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are the rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight and having the same ratio of A blocks to B blocks. Diblocks with a different ratio of A to B blocks or a molecular weight larger or greater than one-half of triblock copolymers may be suitable for improving the foam polymer formula for producing low-density, soft, flexible, absorbent foam via polymer extrusion.

Suitably, the foam polymer formula includes up to about 90%, by weight, of polystyrene, and at least 10%, by weight, of thermoplastic elastomer. More particularly, the foam polymer formula may include between about 45% and about 90%, by weight, of polystyrene, and between about 10% and about 55%, by weight, of thermoplastic elastomer. Alternatively, the foam polymer formula may include between about 50% and about 80%, by weight, of polystyrene, and between about 20% and about 50%, by weight, of thermoplastic elastomer. In one embodiment, for example, the foam polymer formula may include equal amounts of polystyrene and thermoplastic elastomer.

In another embodiment, the foam polymer formula may include about 40% to about 80% by weight polystyrene and about 20% to about 60% by weight thermoplastic elastomer. In another embodiment, the foam polymer formula may include about 50% to about 70% by weight polystyrene and about 30% to about 50% by weight thermoplastic elastomer.

In accordance with the embodiment, a plasticizing agent can be included in the foam polymer formula. A plasticizing agent is a chemical agent that imparts flexibility, stretchability and workability. The type of plasticizing agent has an influence on foam gel properties, blowing agent migration resistance, cellular structure, including the fine cell size, and number of open cells. Typically plasticizing agents are of low molecular weight. The increase in polymer chain mobility and free volume caused by incorporation of a plasticizing agent typically results in a Tg decrease, and plasticizing agent effectiveness is often characterized by this measurement. Petroleum-based oils, fatty acids, and esters are commonly used and act as external plasticizing agents or solvents because they do not chemically bond to the polymer yet remain intact in the polymer cellular structure upon crystallization.

The plasticizing agent increases cell connectivity by thinning membranes between cells to the point of creating porous connections between cells; thus, the plasticizing agent increases open-cell content. Suitably, the plasticizing agent is included in an amount between about 0.5% and about 10%, or between about 1% and about 10%, by weight, of the foam polymer formula. The plasticizing agent is gradually and carefully metered in increasing concentration into the foam polymer formula during the foaming process because too much plasticizing agent added at once creates cellular instability, resulting in cellular collapse.

Examples of suitable plasticizing agents include polyethylene, ethylene vinyl acetate, mineral oil, palm oil, waxes, esters based on alcohols and organic acids, naphthalene oil, paraffin oil, and combinations thereof. A commercially available example of a suitable plasticizing agent is a small-chain polyethylene that is produced as a catalytic polymerization of ethylene; because of its low molecular weight it is often referred to as a "wax." This low-density, highly branched polyethylene "wax" is available from Eastman Chemical Company of Kingsport, Tenn., U.S.A., under the trade designation EPOLENE® C-10.

In a non-limiting embodiment, the first open cell foam, second open cell foam, or both open cell foams may be made from a thermoplastic foam such as a polyurethane foam. The thermoplastic foam may comprise surfactant and plasticizing agent. Polyurethane polymers are generally formed by the reaction of at least one polyisocyanate component and at least one polyol component. The polyisocyanate component may comprise one or more polyisocyanates. The polyol component may comprise one or more polyols. The concentration of a polyol may be expressed with regard to the total polyol component. The concentration of polyol or polyisocyanate may alternatively be expressed with regard to the total polyurethane concentration. Various aliphatic and aromatic polyisocyanates have been described in the art. The polyisocyanate utilized for forming the polyurethane foam typically has a functionality between from 2 and 3. In some embodiments, the functionality is no greater than about 2.5.

In one embodiment, the foam is prepared from at least one aromatic polyisocyanate. Examples of aromatic polyisocyanates include those having a single aromatic ring such as are toluene 2,4 and 2,6-diisocyanate (TDI) and naphthylene 1,5-diisocyanate; as well as those having at least two aromatic rings such as diphenylmethane 4,4'-, 2,4'- and 2,2'-diisocyanate (MDI).

In favored embodiments, the foam is prepared from one or more (e.g. aromatic) polymeric polyisocyanates. Polymeric polyisocyanates typically have a (weight average) molecular weight greater than a monomeric polyisocyanate (lacking repeating units), yet lower than a polyurethane prepolymer. Thus, the polyurethane foam is derived from at least one polymeric polyisocyanate that lacks urethane linkages. In other words, the polyurethane foam is derived from a polymeric isocyanate that is not a polyurethane prepolymer. Polymeric polyisocyanates comprises other linking groups between repeat units, such as isocyanurate groups, biuret groups, carbodiimide groups, uretonimine groups, uretdione groups, etc. as known in the art.

Some polymeric polyisocyanates may be referred to as "modified monomeric isocyanate". For example pure 4,4'-methylene diphenyl diisocyanate (MDI) is a solid having a melting point of 38° C. and an equivalent weight of 125 g/equivalent. However, modified MDIs, are liquid at 38° C. and have a higher equivalent weight (e.g. 143 g/equivalent). The difference in melting point and equivalent weight is believed to be a result of a small degree of polymerization, such as by the inclusion of linking groups, as described above.

Polymeric polyisocyanates, including modified monomeric isocyanate, may comprise a mixture of monomer in combination with polymeric species inclusive of oligomeric species. For example, polymeric MDI is reported to contain 25-80% monomeric 4,4'-methylene diphenyl diisocyanate as well as oligomers containing 3-6 rings and other minor isomers, such as 2,2' isomer.

Polymeric polyisocyanates typically have a low viscosity as compared to prepolymers. The polymeric isocyanates utilized herein typically have a viscosity no greater than about 300 cps at 25° C. and in some embodiments no greater than 200 cps or 100 cps at 25° C. The viscosity is typically at least about 10, 15, 20 or 25 cps at 25° C.

The equivalent weight of polymeric polyisocyanates is also typically lower than that of prepolymers. The polymeric isocyanates utilized herein typically have an equivalent weight of no greater than about 250 g/equivalent and in some embodiments no greater than 200 g/equivalent or 175 g/equivalent. In some embodiments, the equivalent weight is at least 130 g/equivalent.

The average molecular weight (Mw) of polymeric polyisocyanates is also typically lower than that of polyurethane prepolymers. The polymeric isocyanates utilized herein typically have an average molecular weight (Mw) of no greater than about 500 Da and in some embodiments no greater than 450, 400, or 350 Da. In some embodiments, the polyurethane is derived from a single polymeric isocyanate or a blend of polymeric isocyanates. Thus, 100% of the isocyanate component is polymeric isocyanate(s). In other embodiments, a major portion of the isocyanate component is a single polymeric isocyanate or a blend of polymeric isocyanates. In these embodiments, at least 50, 60, 70, 75, 80, 85 or 90 wt-% of the isocyanate component is polymeric isocyanate(s).

Some illustrative polyisocyanates include for example, polymeric MDI diisocyanate from Huntsman Chemical Company, The Woodlands, Tex., under the trade designation "RUBINATE 1245"; and modified MDI isocyanate available from Huntsman Chemical Company under the trade designation "SUPRASEC 9561".

The aforementioned isocyanates are reacted with a polyol to prepare the polyurethane foam material. The polyurethane foams are hydrophilic, such that the foam absorbs aqueous liquids, particularly body fluids. The hydrophilicity of the polyurethane foams is typically provided by use of an isocyanate-reactive component, such as a polyether polyol, having a high ethylene oxide content.

Examples of useful polyols include adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide). Polyols having a high ethylene oxide content can also be made by other techniques as known in the art. Suitable polyols typically have a molecular weight (Mw) of 100 to 5,000 Da and contain an average functionality of 2 to 3.

The polyurethane foam is typically derived from (or in other words is the reaction product of) at least one polyether polyol having ethylene oxide (e.g. repeat) units. The polyether polyol typically has an ethylene oxide content of at least 10, 15, 20 or 25 wt-% and typically no greater than 75 wt-%. Such polyether polyol has a higher functionality than the polyisocyanate. In some embodiments, the average functionality is about 3. The polyether polyol typically has a viscosity of no greater than 1000 cps at 25° C. and in some embodiments no greater than 900, 800, or 700 cps. The molecular weight of the polyether polyol is typically at least 500 or 1000 Da and in some embodiments no greater than 4000 or 3500, or 3000 Da. Such polyether polyol typically has a hydroxyl number of at least 125, 130, or 140. An illustrative polyol includes for example a polyether polyol product obtained from the Carpenter Company, Richmond, Va. under the designation "CDB-33142 POLYETHER POLYOL", "CARPOL GP-5171".

In some embodiments, one or more polyether polyols having a high ethylene oxide content and a molecular weight (Mw) of no greater than 5500, or 5000, or 4500, or 4000, or 3500, or 3000 Da, as just described, are the primary or sole polyether polyols of the polyurethane foam. For example, such polyether polyols constitute at least 50, 60, 70, 80, 90, 95 or 100 wt-% of the total polyol component. Thus, the polyurethane foam may comprise at least 25, 30, 35, 40, 45 or 50 wt-% of polymerized units derived from such polyether polyols.

In other embodiments, one or more polyether polyols having a high ethylene oxide content are utilized in combination with other polyols. In some embodiments, the other polyols constitute at least 1, 2, 3, 4, or 5 wt-% of the total polyol component. The concentration of such other polyols typically does not exceed 40, or 35, or 30, or 25, or 20, or 15, or 10 wt-% of the total polyol component, i.e. does not exceed 20 wt-%, or 17.5 wt-%, or 15 wt-%, or 12.5 wt-%, or 10 wt-%, or 7.5 wt-%, or 5 wt-% of the polyurethane. Illustrative other polyols include a polyether polyol product (Chemical Abstracts Number 25791-96-2) that can be obtained from the Carpenter Company, Richmond, Va. under the designation "CARPOL GP-700 POLYETHER POLYOL" and a polyether polyol product (Chemical Abstracts Number 9082-00-2) that can be obtained from Bayer Material Science, Pittsburgh, Va. under the trade designation "ARCOL E-434". In some embodiments, such optional other polyols may comprise polypropylene (e.g. repeat) units.

The polyurethane foam generally has an ethylene oxide content of at least 10, 11, or 12 wt-% and no greater than 20, 19, or 18 wt-%. In some embodiments, the polyurethane foam has an ethylene oxide content of no greater than 17 or 16 wt-%.

The kinds and amounts of polyisocyanate and polyol components are selected such that the polyurethane foam is relatively soft, yet resilient. These properties can be characterized for example by indentation force deflection and constant deflection compression set, as measured according to the test methods described in the examples. In some embodiments, the polyurethane foam has an indentation force deflection of less than 75N at 50%. The indentation force deflection at 50% may be less than 70N, or 65N, or 60 N. In some embodiments, the polyurethane foam has an indentation force deflection of less than 100N at 65%. The indentation force deflection at 65% may be less than 90N, or 80N, or 70 N, or 65N, or 60N. In some embodiments, the indentation force deflection at 50% or 65% is typically at least 30N or 35N. The constant deflection compression set at 50% deflection can be zero and is typically at least 0.5, 1 or 2% and generally no greater than 35%. In some embodiments, the constant deflection compression set at 50% deflection is no greater than 30%, or 25%, or 20%, or 15%, or 10%.

The polyurethane foam may comprise known and customary polyurethane formation catalysts such as organic tin compounds and/or an amine-type catalyst. The catalysts are preferably used in an amount of from 0.01 to 5 wt-% of the polyurethane. The amine-type catalyst is typically a tertiary amine. Examples of suitable tertiary amine include monoamines such as triethylamine, and dimethyl cyclohexylamine; diamines such as tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,5-diazabicyclo(5,4,0)undecene-7 (DBU), and 1,5-diazabicyclo(4,3,0)nonene-5; and organic acid salts of the diazabicycloalkenes such as phenol salt, 2-ethylhexanoate and formate of DBU. These amines can be used either singly or in combination. The amine-type catalyst can be used in an amount no greater than 4, 3, 2, 1 or 0.5 wt-% of the polyurethane.

The polyurethane typically comprises a surfactant to stabilize the foam. Various surfactants have been described in the art. In one embodiment a silicone surfactant is employed that comprises ethylene oxide (e.g. repeat) units, optionally in combination with propylene oxide (e.g. repeat) units such as commercially available from Air Products under the trade designation "DABCO DC-198". In some embodiments, the concentration of hydrophilic surfactant typically ranges from about 0.05 to 1 or 2 wt-% of the polyurethane.

The polyurethane foam may comprise various additives such as surface active substances, foam stabilizers, cell regulators, blocking agents to delay catalytic reactions, fire retardants, chain extenders, crosslinking agents, external and internal mold release agents, fillers, pigments (titanium dioxide), colorants, optical brighteners, antioxidants, stabilizers, hydrolysis inhibitors, as well as anti-fungal and anti-bacteria substances. Such other additives are typically collectively utilized at concentrations ranging from 0.05 to 10 wt-% of the polyurethane.

In some embodiments, the absorbent foam is white in color. Certain hindered amine stabilizers can contribute to discoloration, such as yellowing, of the absorbent foam. In some embodiments, the absorbent foam is free of diphenylamine stabilizer and/or phenothiazine stabilizer.

In other embodiments, the absorbent foam may be a colored (i.e. a color other than white). The white or colored absorbent foam can include a pigment in at least one of the components. In preferred embodiments, pigment is combined with a polyol carrier and is added to the polyol liquid stream during manufacture of the polyurethane foam. Commercially available pigments include for example DispersiTech™ 2226 White, DispersiTech™ 2401 Violet, DispersiTech™ 2425 Blue, DispersiTech™ 2660 Yellow, and DispersiTech™ 28000 Red from Milliken in Spartansburg, S.C. and Pdi® 34-68020 Orange from Ferro in Cleveland, Ohio.

In the production of polyurethane foams, the polyisocyanate component and polyol component are reacted such that an equivalence ratio of isocyanate groups to the sum of hydroxyl groups is no greater than 1 to 1. In some embodiments, the components are reacted such that there are excess hydroxyl groups (e.g. excess polyol). In such embodiments, the equivalence ratio of isocyanate groups to the sum of the hydroxy groups is at least 0.7 to 1. For example, the ratio may be at least 0.75:1, or at least 0.8:1.

The hydrophilic (e.g. polyol(s)) component(s) of the (e.g. polyurethane) polymeric foam provide the desired absorption capacity of the foam. Thus the foam may be free of superabsorbent polymer. Further, the polyurethane foam is free of amine or imine complexing agent such as ethylenimine, polyethylenimine, polyvinylamine, carboxy-methylated polyethylenimines, phosphono-methylated polyethylenimines, quaternized polyethylenimines and/or dithiocarbamitized polyethylenimines; as described for example in U.S. Pat. No. 6,852,905 and 6,855,739.

The polymeric (e.g. polyurethane) foam typically has an average basis weight of at least 100, 150, 200, or 250 gsm and typically no greater than 500 gsm. In some embodiments the average basis weight is no greater than 450, or 400 gsm. The average density of the (e.g. polyurethane) polymeric foam is typically at least 3, 3.5 or 4 lbs/ft$^3$ and no greater than 7 lbs/ft$^3$.

In a non-limiting embodiment, the first open cell foam, second open cell foam, or both open cell foams may be a High Internal Phase Emulsion (HIPE) foam, also referred to as a polyHIPE foam. To form a HIPE, an aqueous phase and an oil phase are combined in a ratio between about 8:1 and 140:1. In certain embodiments, the aqueous phase to oil phase ratio is between about 10:1 and about 75:1, and in certain other embodiments the aqueous phase to oil phase ratio is between about 13:1 and about 65:1. This is termed the "water-to-oil" or W:O ratio and can be used to determine the density of the resulting polyHIPE foam. As discussed, the oil phase may contain one or more of monomers, comonomers, photoinitiators, crosslinkers, and emulsifiers, as well as optional components. The water phase will contain water and in certain embodiments one or more components such as electrolyte, initiator, or optional components.

The HIPE can be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, and in certain embodiments, after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE can then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The HIPE can be infused into the cellular structure thereby filling at least a portion of the cellular structure prior to being fully polymerized. Once fully polymerized, the HIPE and the cellular structure forms a foam composite wherein a first foam provides the cellular structure containing the HIPE foam.

Following polymerization, the resulting foam pieces are saturated with aqueous phase that needs to be removed to obtain substantially dry foam pieces. In certain embodiments, foam pieces can be squeezed free of most of the aqueous phase by using compression, for example by running the absorbent structure comprising the foam pieces through one or more pairs of nip rollers. The nip rollers can be positioned such that they squeeze the aqueous phase out of the foam pieces. The nip rollers can be porous and have a vacuum applied from the inside such that they assist in drawing aqueous phase out of the foam pieces. In certain embodiments, nip rollers can be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller can be pressurized while the other, for example the second nip roller, can be evacuated, so as to both blow and draw the aqueous phase out the of the foam. The nip rollers may also be heated to assist in removing the aqueous phase. In certain embodiments, nip rollers are only applied to non-rigid foams, that is, foams whose walls would not be destroyed by compressing the foam pieces.

In certain embodiments, in place of or in combination with nip rollers, the aqueous phase may be removed by sending the foam pieces through a drying zone where it is heated, exposed to a vacuum, or a combination of heat and vacuum exposure. Heat can be applied, for example, by running the foam though a forced air oven, IR oven, microwave oven or radiowave oven. The extent to which a foam is dried depends on the application. In certain embodiments, greater than 50% of the aqueous phase is removed. In certain other embodiments greater than 90%, and in still other embodiments greater than 95% of the aqueous phase is removed during the drying process.

In an embodiment, open cell foam is produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. In certain embodiments, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type can have styrene and vinyl chloride.

The oil phase may further contain an emulsifier used for stabilizing the HIPE. Emulsifiers used in a HIPE can include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they can have between about 1% and about 20%, in certain embodiments from about 2% to about 15%, and in certain other embodiments from about 3% to about 12% by weight of the oil phase. In certain embodiments, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. In certain embodiments, ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Specialty Chemicals, Ludwigshafen, Germany as DAROCUR® 4265); benzyl dimethyl ketal (sold by Ciba as IRGACURE 651); α-,α-dimethoxy-α-hydroxy acetophenone (sold by Ciba Specialty Chemicals as DAROCUR® 1173); 2-methyl-1-[4-(methyl thio)phenyl]-2-morpholino-propan-1-one (sold by Ciba Specialty Chemicals as IRGACURE® 907); 1-hydroxycyclohexyl-phenyl ketone (sold by Ciba Specialty Chemicals as IRGACURE® 184); bis(2,4,6-trimethylbenzoyl)-phenylphosphineoxide (sold by Ciba Specialty Chemicals as IRGACURE 819); diethoxyacetophenone, and 4-(2-hydroxyethoxy)phenyl-(2-hydroxy-2-methylpropyl)ketone (sold by Ciba Specialty Chemicals as IRGACURE® 2959); and Oligo [2-hydroxy-2-methyl-1-[4-(1-methylvinyl)phenyl]propanone] (sold by Lambeth spa, Gallarate, Italy as ESACURE® KIP EM.

The dispersed aqueous phase of a HIPE can have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. In certain embodiments, to reduce the potential for premature polymerization which may clog the emulsification system, addition of the initiator to the monomer phase may be just after or near the end of emulsification.

Photoinitiators present in the aqueous phase may be at least partially water soluble and can have between about 0.05% and about 10%, and in certain embodiments between about 0.2% and about 10% by weight of the aqueous phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane] disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The absorbent structure may additionally comprise additional foams such as a third open cell foam. The additional foam may be made of any of the previously mentioned foams such as, for example, a HIPE foam or a polyurethane foam. The additional foam may be different in composition, cell size range, or any other property of the foam from the first or the second open cell foam in the absorbent structure.

However structured, the total absorbent capacity of the absorbent structure should be compatible with the design loading and the intended use of the mass. For example, when used in an absorbent article, the size and absorbent capacity of the absorbent structure may be varied to accommodate different uses such as incontinence pads, pantiliners, regular sanitary napkins, or overnight sanitary napkin.

The absorbent structure produced from the present invention may be used as an absorbent core or a portion of an absorbent core in absorbent articles, such as feminine hygiene articles, for example pads, pantiliners, and tampons; disposable diapers; incontinence articles, for example pads, adult diapers; homecare articles, for example wipes, pads, wound dressings, towels; and beauty care articles, for example pads, wipes, and skin care articles, such as used for pore cleaning.

In one embodiment the absorbent structure may be used as an absorbent core for an absorbent article. In such an embodiment, the absorbent core can be relatively thin, less than about 5 mm in thickness, or less than about 3 mm, or less than about 1 mm in thickness. Cores having a thickness of greater than 5 mm are also contemplated herein. Thickness can be determined by measuring the thickness at the midpoint along the longitudinal centerline of the pad by any means known in the art for doing while under a uniform pressure of 0.25 psi. The absorbent core can comprise absorbent gelling materials (AGM), including AGM fibers, as is known in the art.

The absorbent structure may be formed or cut to a shape, the outer edges of which define a periphery. Additionally, the absorbent structure may be continuous such that it may be rolled or wound upon itself, with or without the inclusion of preformed cut lines demarcating the absorbent structure into preformed sections.

When used as an absorbent core, the shape of the absorbent structure can be generally rectangular, circular, oval, elliptical, or the like. Absorbent core can be generally centered with respect to the longitudinal centerline and transverse centerline of an absorbent article. The profile of absorbent core can be such that more absorbent is disposed near the center of the absorbent article. For example, the absorbent core can be thicker in the middle, and tapered at the edges in a variety of ways known in the art.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

In at least one embodiment, at least the first open cell foam or the second open cell foam comprises a bio-based content value from about 10% to about 100% using ASTM D6866-10, method B, in another embodiment, from about 25% to about 75%, and in yet another embodiment, from about 50% to about 60%. Foam pieces may be made from bio-based content such as monomers as described in US2012/0108692 A1 Dyer published May 3, 2012.

In order to apply the methodology of ASTM D6866-10 to determine the bio-based content of any foam piece, a representative sample of the foam piece must be obtained for testing. In at least one embodiment, the foam piece can be ground into particulates less than about 20 mesh using known grinding methods (e.g., Wiley® mill), and a representative sample of suitable mass taken from the randomly mixed particles.

Validation of Polymers Derived from Renewable Resources

A suitable validation technique is through $^{14}C$ analysis. A small amount of the carbon dioxide in the atmosphere is radioactive. This $^{14}C$ carbon dioxide is created when nitrogen is struck by an ultra-violet light produced neutron, causing the nitrogen to lose a proton and form carbon of molecular weight 14 which is immediately oxidized to carbon dioxide. This radioactive isotope represents a small but measurable fraction of atmospheric carbon. Atmospheric carbon dioxide is cycled by green plants to make organic molecules during photosynthesis. The cycle is completed when the green plants or other forms of life metabolize the organic molecules, thereby producing carbon dioxide which is released back to the atmosphere. Virtually all forms of life on Earth depend on this green plant production of organic molecules to grow and reproduce. Therefore, the $^{14}C$ that exists in the atmosphere becomes part of all life forms, and their biological products. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the bio-based content of materials can be determined. ASTM International, formally known as the American Society for Testing and Materials, has established a standard method for assessing the bio-based content of materials. The ASTM method is designated ASTM D6866-10.

The application of ASTM D6866-10 to derive a "bio-based content" is built on the same concepts as radiocarbon dating, but without use of the age equations. The analysis is performed by deriving a ratio of the amount of organic radiocarbon ($^{14}C$) in an unknown sample to that of a modern reference standard. The ratio is reported as a percentage with the units "pMC" (percent modern carbon).

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, for example, it would give a radiocarbon signature near 54 pMC (assuming the petroleum derivatives have the same percentage of carbon as the soybeans).

A biomass content result is derived by assigning 100% equal to 107.5 pMC and 0% equal to 0 pMC. In this regard, a sample measuring 99 pMC will give an equivalent bio-based content value of 92%.

Assessment of the materials described herein can be done in accordance with ASTM D6866. The mean values quoted in this report encompasses an absolute range of 6% (plus and minus 3% on either side of the bio-based content value) to account for variations in end-component radiocarbon signatures. It is presumed that all materials are present day or fossil in origin and that the desired result is the amount of biobased component "present" in the material, not the amount of biobased material "used" in the manufacturing process.

The absorbent structure may serve as any portion of an absorbent article. In an embodiment, the absorbent structure may serve as the absorbent core of an absorbent article. In an embodiment, the absorbent structure may serve as a portion of the absorbent core of an absorbent article. In an embodiment, more than one absorbent structure may be combined wherein each absorbent structure differs from at least one other absorbent structure in either the choice of open cell foams or in the characteristics of the open cell foams. The different two or more absorbent structures may be combined to form an absorbent core. The absorbent article may further comprise a topsheet and a backsheet.

In an embodiment, the absorbent structure may be combined with any other type of absorbent layer such as, for example, a layer of cellulose, a layer comprising superabsorbent gelling materials, a layer of absorbent airlaid fibers, a layer of spunlace fibers, or a layer of absorbent foam. Other absorbent layers not listed are contemplated herein. In an embodiment, the absorbent structure may comprise superabsorbents.

Spunlace fibers may be carded staple fibers that can be manufactured from an assortment of suitable fiber types that produce the desired mechanical performance and fluid handling performance. In some embodiments, the carded staple fibers may be formed from a combination of stiffening fibers, absorbing fibers and filler fibers, as further detailed in U.S. Provisional Patent Application No. 62/008,677, filed on Jun. 6, 2014.

In an embodiment, the absorbent structure may be utilized by itself for the absorption of fluids without placing it into an absorbent article.

According to an embodiment, an absorbent article can comprise a liquid pervious topsheet. The topsheet suitable for use herein can comprise wovens, non-wovens, and/or three-dimensional webs of a liquid impermeable polymeric film comprising liquid permeable apertures. The topsheet for use herein can be a single layer or may have a multiplicity of layers. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. No. 3,929,135, 4,151,240, 4,319,868, 4,324,426, 4,343,314, 4,591,523, 4,609,518, 4,629,643, 4,695,422 or WO 96/00548.

Especially when the absorbent article finds utility as a sanitary napkin or panty liner, the absorbent article can be also provided with a panty fastening means, which provides means to attach the article to an undergarment, for example a panty fastening adhesive on the garment facing surface of the backsheet. Wings or side flaps meant to fold around the crotch edge of an undergarment can be also provided on the side edges of the napkin.

FIG. 1 shows a SEM micrograph of a cross section of an absorbent structure 10 having a HIPE foam 20 associated with a polyurethane foam 30 taken at 15× magnification. As show in the figure, the polyurethane foam 30 provides a cellular structure that contains the HIPE foam 20.

Figure 2:
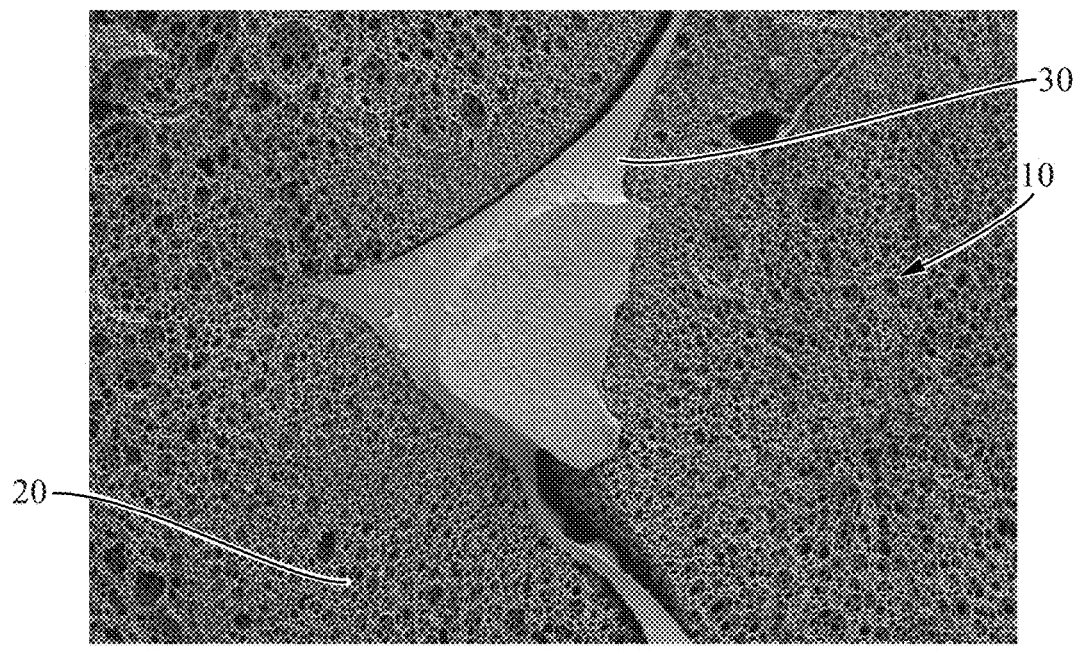
FIG. 2 shows a magnified cross section view of a foam cellular structure containing a HIPE foam.

FIG. 2 shows a SEM micrograph of a cross section of an absorbent structure 10 having a HIPE foam 20 associated with a polyurethane foam 30 taken at 300× magnification. As shown in FIG. 2 and FIG. 1, the polyurethane foam 30 provides a cellular structure that contains the HIPE foam 20. The HIPE foam 20 fills the voids in the open cell polyurethane 30.

Figure 3:
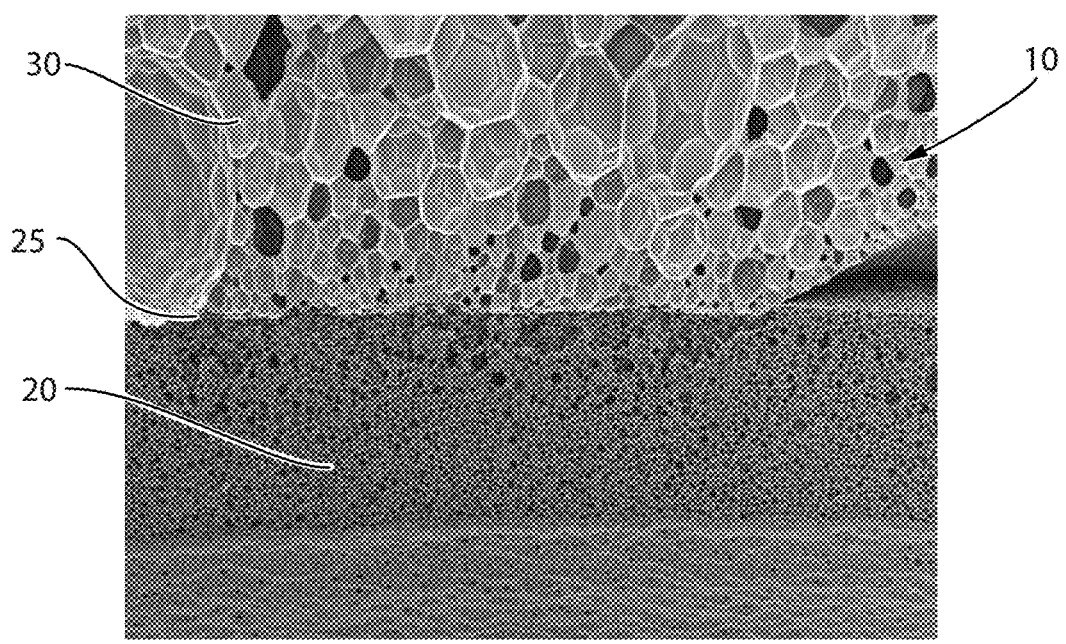
FIG. 3 is a magnified cross section view of a HIPE foam associated with a polyurethane foam.

FIG. 3 shows a SEM micrograph of a cross section of an absorbent structure 10 having a HIPE foam 20 associated with a polyurethane foam 30 taken at 15× magnification. As shown in FIG. 3, the polyurethane foam 30 is associated with the HIPE foam 20 at an interface 25 such that the materials are in direct contact.

Figure 4:
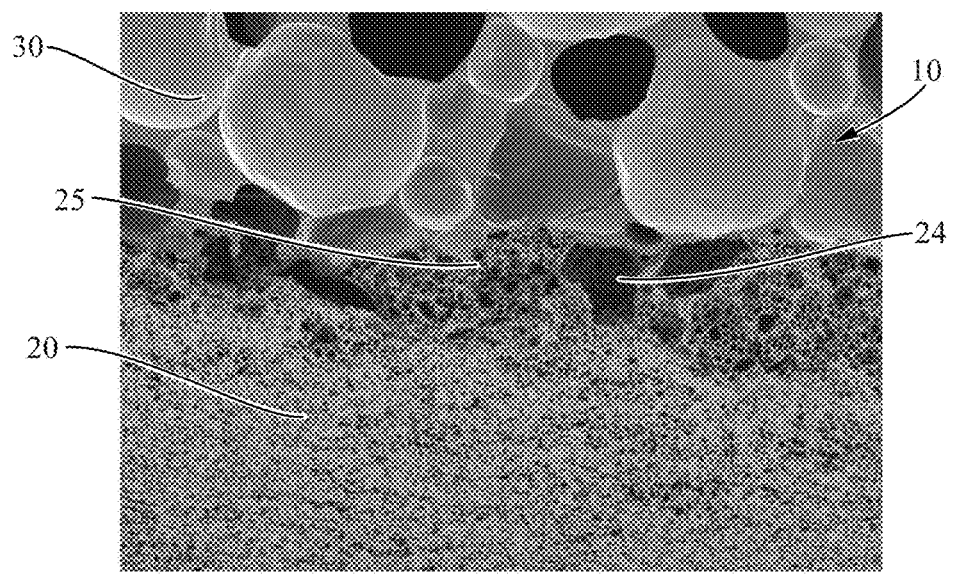
FIG. 4 is a magnified view of the SEM of FIG. 3.

FIG. 4 shows a SEM micrograph of a cross section of an absorbent structure 10 having a HIPE foam 20 associated with a polyurethane foam 30 taken at 200× magnification. As shown in FIG. 4, the polyurethane foam 30 is associated with the HIPE foam 20 at an interface 25 such that the polyurethane foam 30 penetrates the HIPE foam 20 and expands the HIPE foam while polymerizing to create fractures 24 in the HIPE foam structure.

Figure 5:
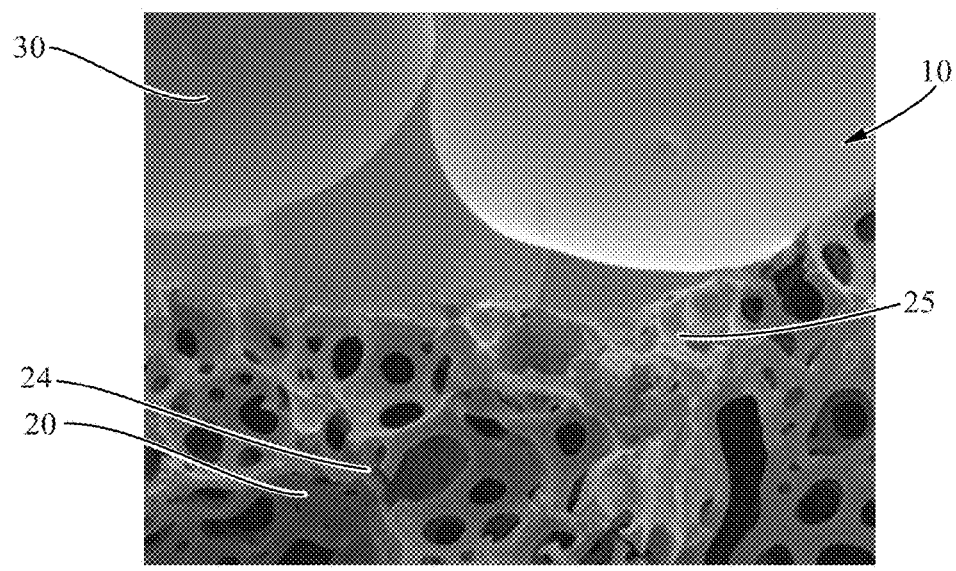
FIG. 5 is a magnified cross section view of a HIPE foam associated with a polyurethane foam.

FIG. 5 shows a SEM micrograph of a cross section of an absorbent structure 10 having a HIPE foam 20 associated with a polyurethane foam 30 taken at 2500× magnification. As shown in FIG. 5, the polyurethane foam 30 is associated with the HIPE foam 20 at an interface 25 such that the polyurethane foam 30 penetrates the HIPE foam 20 and expands the HIPE foam while polymerizing to create fractures 24 in the HIPE foam structure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising
    a first open cell foam having a first surface and a second surface and a second open cell foam, wherein the first open cell foam is associated with the second open cell foam,
    wherein the second open cell foam is an acrylate based High Internal Phase Emulsion foam, wherein the first open cell foam comprises a thermoplastic polymer foam, wherein the first open cell foam provides a cellular structure comprising the second open cell foam, and wherein the second open cell foam is inserted into and surrounded by the first open cell foam.

2. The absorbent structure of claim 1, wherein the size of the second open cell foam pores are between 0.03% and 99% of the size of the first open cell foam pores.

3. The absorbent structure of claim 1, wherein the cellular structure further comprises a third open cell foam.

4. The absorbent structure of claim 1, wherein the absorbent structure is used as an absorbent core for an absorbent article.

5. The absorbent structure of claim 1, wherein the first open cell foam or the second open cell foam comprises a bio-based content value from about 10% to about 100% using ASTM D6866-10, method B.

6. An absorbent article comprising a topsheet, a backsheet, and an absorbent core wherein the absorbent core comprises an absorbent structure comprising a first open cell foam having a first surface and a second surface and a second open cell foam, wherein the first open cell foam is associated with the second open cell foam, wherein the second open cell foam is an acrylate based High Internal Phase Emulsion foam, wherein the first open cell foam comprises a thermoplastic polymer foam, wherein the first open cell foam provides a cellular structure comprising the second open cell foam, wherein the second open cell foam is inserted into and surrounded by the first open cell foam.

7. The absorbent article of claim 6, wherein the size of the second open cell foam pores are between 0.03% and 99% of the size of the first open cell foam pores.

8. The absorbent article of claim 6, wherein the cellular structure further comprises a third open cell foam.

9. The absorbent article of claim 6, wherein the first open cell foam or the second open cell foam comprises a bio-based content value from about 10% to about 100% using ASTM D6866-10, method B.

* * * * *